(12) United States Patent
Ofer

(10) Patent No.: US 11,712,191 B2
(45) Date of Patent: *Aug. 1, 2023

(54) METHODS AND SYSTEMS FOR TRANSFORMATION BETWEEN EYE IMAGES AND DIGITAL IMAGES

(71) Applicant: Moshe Ofer, Ramat Hasharon (IL)

(72) Inventor: Moshe Ofer, Ramat Hasharon (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/740,425

(22) Filed: May 10, 2022

(65) Prior Publication Data

US 2022/0386937 A1 Dec. 8, 2022

Related U.S. Application Data

(63) Continuation of application No. 17/534,622, filed on Nov. 24, 2021, now Pat. No. 11,395,620.

(60) Provisional application No. 63/196,274, filed on Jun. 3, 2021.

(51) Int. Cl.
*A61B 5/00* (2006.01)
*A61B 5/378* (2021.01)

(52) U.S. Cl.
CPC ............ *A61B 5/4064* (2013.01); *A61B 5/378* (2021.01); *A61B 5/4047* (2013.01); *A61B 5/4076* (2013.01); *A61B 5/6868* (2013.01)

(58) Field of Classification Search
CPC ..... A61B 5/4064; A61B 5/378; A61B 5/4047; A61B 5/4076; A61B 5/6868; A61B 5/291; A61B 5/398; A61B 5/375; A61B 5/16; A61B 5/369; A61N 1/0456; A61N 1/36025; A61H 2205/024; A61H 2230/10

See application file for complete search history.

(56) References Cited

U.S. PATENT DOCUMENTS

| | | | |
|---|---|---|---|
| 6,175,767 B1 | 1/2001 | Doyle, Sr. | |
| 7,991,475 B1 | 8/2011 | Tang et al. | |
| 8,369,958 B2 | 2/2013 | Kwon et al. | |
| 10,123,133 B2 | 11/2018 | Pontoppidan et al. | |
| 2008/0161915 A1 | 7/2008 | Ren | |
| 2009/0216091 A1 | 8/2009 | Arndt | |
| 2014/0267401 A1 | 9/2014 | Urbach | |

FOREIGN PATENT DOCUMENTS

| | | |
|---|---|---|
| CN | 103705229 A | 4/2014 |
| CN | 204520668 U | 8/2015 |

*Primary Examiner* — Patrick Fernandes
(74) *Attorney, Agent, or Firm* — Mark M. Friedman

(57) ABSTRACT

A processing device receives signals associated with nerve impulses that are transmitted to the visual cortex of a subject in response to one or more visual stimuli provided to at least one eye of the subject. The processing device processes the received signals and generates digital image data from the processed received signals that is representative of the visual perception, by the subject, of the one or more visual stimuli. In certain embodiments, the processing device processes digital image data that is representative of a scene to convert the digital image data to a sequence of nerve impulses, and provides the sequence of nerve impulses to the visual cortex of a subject such that the subject visually perceives the scene.

17 Claims, 3 Drawing Sheets

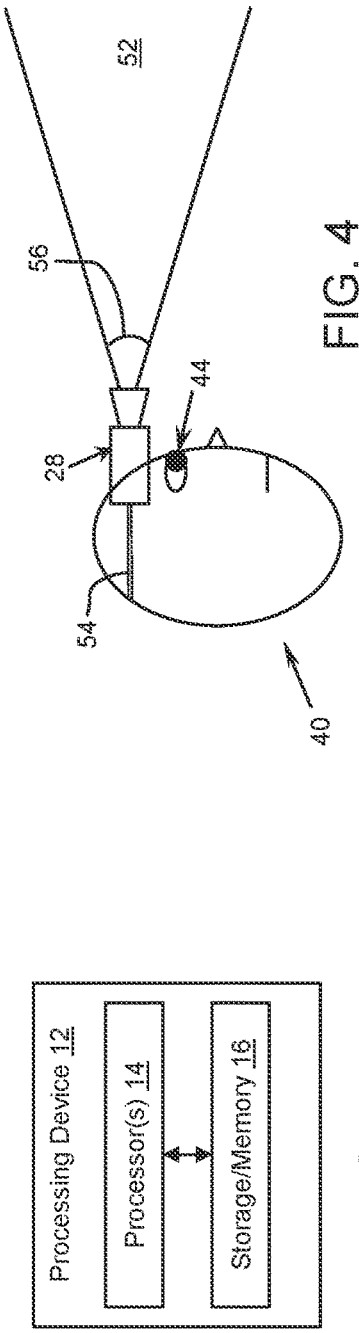
FIG. 2
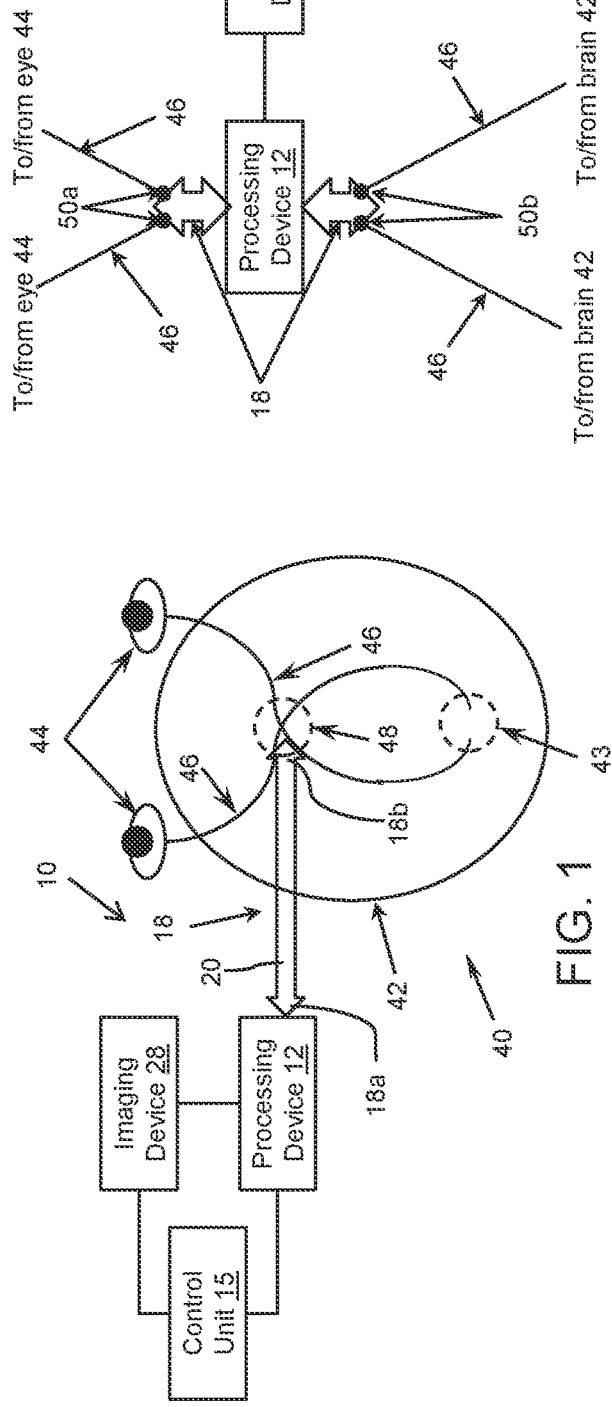
FIG. 1
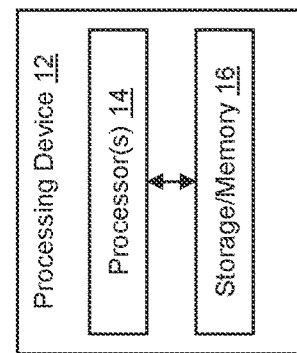
FIG. 3
FIG. 4

METHODS AND SYSTEMS FOR TRANSFORMATION BETWEEN EYE IMAGES AND DIGITAL IMAGES

CROSS-REFERENCE TO RELATED APPLICATIONS

This application claims priority from U.S. Provisional Patent Application No. 63/196,274, filed Jun. 3, 2021, whose disclosure is incorporated by reference in its entirety herein.

TECHNICAL FIELD

The present invention relates to vision, and more particularly the routing of digital images to and from the brain.

BACKGROUND OF THE INVENTION

The human vision system comprises the eyes, the brain, and parts of the nervous system. In general, light is sensed by photoreceptors (rods and cones) in the eye, and are converted into nerve impulses that are transmitted to the brain by the optic nerve, to be interpreted by the brain as sight and vision.

SUMMARY OF THE INVENTION

According to the teachings of an embodiment of the present invention, there is provided a method that comprises: receiving, by a processing device, signals associated with nerve impulses transmitted to the visual cortex of a subject in response to one or more visual stimuli provided to at least one eye of the subject; and processing, by the processing device, the received signals to generate digital image data representative of the visual perception, by the subject, of the one or more visual stimuli.

Optionally, the method further comprises: performing at least one operation on the generated digital image data according to one or more rules.

Optionally, the at least one operation includes: storing some or all of the generated digital image data in a computerized storage device associated with the processing device.

Optionally, the at least one operation includes: sending some or all of the generated digital image data to a computerized server system over one or more communication networks.

Optionally, the at least one operation includes: modifying the generated digital image data to generate modified digital image data.

Optionally, the modifying includes at least one of: i) augmenting the generated digital image data by incorporating additional digital image data into the generated digital image data, or ii) changing at least one pixel value of the generated digital image data.

Optionally, the method further comprises: converting the modified digital image data into one or more nerve impulses; and providing the one or more nerve impulse to the visual cortex so as to augment the visual perception, by the subject, of the one or more visual stimuli.

Optionally, providing the one or more nerve impulses to the visual cortex includes inducing one or more nerves associated with the visual cortex to transmit the one or more nerve impulses by stimulating one or more neurons of the one or more nerves to generate the nerve impulses.

Optionally, processing the received signals includes: applying to the received signals at least one mapping that maps between nerve impulses and digital image data.

Optionally, the method further comprises: generating the at least one mapping.

Optionally, the method further comprises: deploying the processing device in communication with the visual cortex of the subject, the deploying includes an operation selected from the group consisting of: i) surgically implanting the processing device at or on a segment of at least one nerve associated with the visual cortex, ii) surgically implanting the processing device at or on the visual cortex, iii) surgically implanting at least a portion of a machine-subject interface, that places the processing device in communication with the visual cortex, at or on a segment of at least one nerve associated with the visual cortex, and iv) surgically implanting at least a portion of a machine-subject interface, that places the processing device in communication with the visual cortex, at or on the visual cortex.

Optionally, the method further comprises: measuring, by a microdevice surgically implanted in the subject in association with the visual cortex of the subject, the nerve impulses transmitted by at least one nerve associated with the visual cortex to produce the signals associated with the nerve impulses transmitted to the visual cortex.

There is also provided according to an embodiment of the teachings of the present invention a system that comprises: a processing device for interfacing with the visual cortex of a subject and configured to: receive signals associated with nerve impulses transmitted to the visual cortex in response to one or more visual stimuli provided to at least one eye of the subject, and process the received signals to generate digital image data representative of the visual perception, by the subject, of the one or more visual stimuli.

Optionally, the processing device is further configured to: modify the generated digital image data to generate modified digital image data, and convert the modified digital image data into one or more nerve impulses.

Optionally, the processing device is further configured to: provide the one or more nerve impulses to the visual cortex of the subject so as to augment the visual perception, by the subject, of the one or more visual stimuli.

Optionally, the processing device is configured to provide the one or more nerve impulses to the visual cortex through an interface that places the processing device in communication with the visual cortex, the interface being configured to induce one or more nerves associated with the visual cortex to transmit the one or more nerve impulses to the visual cortex.

Optionally, the processing device is configured to process the received signals by applying at least one mapping that maps between nerve impulses and digital image data.

Optionally, the processing device is further configured to generate the at least one mapping.

Optionally, the system further comprises: at least one memory device associated with the processing device for storing digital image data representative of at least one image, and the processing device being configured to generate the at least one mapping based at least in part on the digital image data stored in the at least one memory device.

Optionally, the system further comprises: an interface for placing the processing device in communication with the visual cortex and for obtaining nerve impulses transmitted to the visual cortex in response to one or more visual stimuli provided to at least one eye of the subject.

There is also provided according to an embodiment of the teachings of the present invention a method that comprises:

processing digital image data representative of a scene using a processing device to convert the digital image data to a sequence of nerve impulses; and providing the sequence of nerve impulses to the visual cortex of a subject such that the subject visually perceives the scene.

Optionally, at least some of the digital image data is provided to the processing device by at least one of: a memory device that stores the digital image data, or an imaging device that generates the digital image data.

There is also provided according to an embodiment of the teachings of the present invention a system that comprises: a processing device for interfacing with the visual cortex of a subject and configured to: process digital image data representative of a scene to convert the digital image data to a sequence of nerve impulses, and provide the sequence of nerve impulses to the visual cortex such that the subject visually perceives the scene.

Optionally, the system further comprises: an imaging device for capturing images, and at least some of the digital image data being generated by the imaging device in response to the imaging device capturing at least one image of the scene There is also provided according to an embodiment of the teachings of the present invention a vision system for augmenting the visual perception by a subject in an environment, the vision system comprises: at least one subject-mounted imaging device deployed to capture images of the environment, each image comprising digital image data representative of the environment; and a processing device for interfacing with the visual cortex of the subject and configured to: process the digital image data to convert the digital image data into a sequence of nerve impulses, and provide the sequence of nerve impulses to at least one nerve associated with the visual cortex so as to induce transmission of the sequence of nerve impulses by the at least one nerve, such that the subject visually perceives the environment.

Unless otherwise defined herein, all technical and/or scientific terms used herein have the same meaning as commonly understood by one of ordinary skill in the art to which the invention pertains. Although methods and materials similar or equivalent to those described herein may be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the present invention are herein described, by way of example only, with reference to the accompanying drawings. With specific reference to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

Attention is now directed to the drawings, where like reference numerals or characters indicate corresponding or like components. In the drawings:

FIG. 1 is a schematic representation of a system having a processing device for interfacing with the visual cortex of a subject and for converting nerve impulses into digital image data and vice versa, and having an imaging device for capturing images of a scene and a control unit associated with the processing device and the imaging device, according to an embodiment of the present invention;

FIG. 2 is a schematic representation of an example deployment of the processing device of FIG. 1 in which the processing device interfaces with the visual cortex via implantation at the optic nerves, according to an embodiment of the present invention;

FIG. 3 is a block diagram of an exemplary processing device, according to an embodiment of the present invention;

FIG. 4 is a schematic representation of an example deployment of the imaging device of FIG. 1 as a head-mounted device, according to an embodiment of the present invention;

DESCRIPTION OF THE PREFERRED EMBODIMENTS

Figure 5:
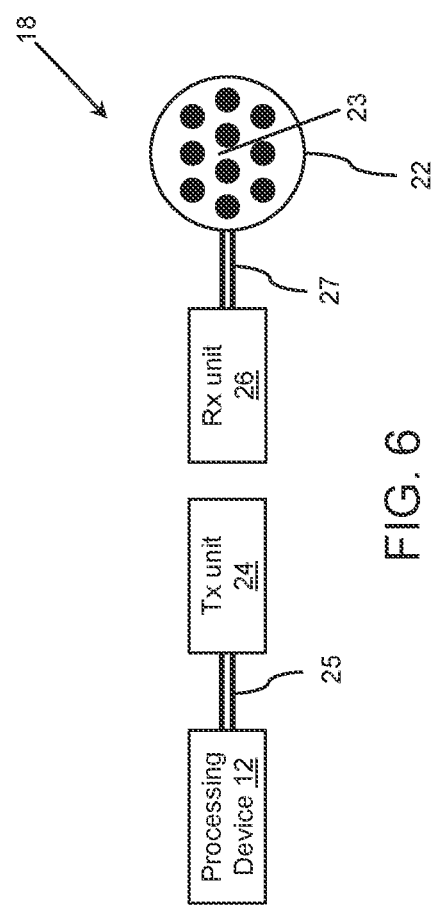
FIG. 5 is a schematic representation of an exemplary wired interface that includes an electrode array that can be used for interfacing between the processing device and the visual cortex of the subject, according to an embodiment of the present invention.

Embodiments of the present invention provide methods and systems for obtaining signals representative of nerve impulses transmitted by the optic nerves and converting those signals into digital image data, and for converting digital images data to corresponding nerve impulses and providing those nerve impulses to the optic nerves for transmission.

The principles and operation of the systems and methods according to present invention may be better understood with reference to the drawings accompanying the description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

Referring now to the drawings, FIG. 1 is a schematic representation of a system, generally designated 10, according to an embodiment of the present invention. Generally speaking, the system 10 includes a computerized processing device 12 (referred to hereinafter interchangeably as "processing device") for interfacing (communicatively coupling)

to the visual cortex 43 of the brain 42 of a subject (also referred to as a "user") 40, for example via at least one nerve 46 illustrated here as a pair of nerves 46. In the illustrated embodiment, the processing device 12 is coupled to at least one of the optic nerves 46, which is a paired cranial nerve that serves as a pathway between the eyes 44 and the brain 42 of the subject 40.

As will be discussed in further detail below, the processing device 12 is operative to receive signals associated with nerve impulses that carry image information and that are transmitted to the visual cortex 43 of the brain 42. This process of receiving signals by the processing device 12 is generally referred to herein as "collecting nerve impulses". The nerve impulses are typically transmitted by the nerves 46, along the path from the eyes 44 to the visual cortex 43 of the brain 42, in response to one or more visual stimuli (light) that are provided to the eyes 44. As discussed in the background, the light corresponding to the visual stimuli is sensed by photoreceptors in the eyes 44, and are converted into nerve impulses that are transmitted to the brain 42 by the optic nerves 46, to be interpreted by the brain 42 as sight and vision. This interpretation of nerve impulses by the brain 42 is referred to herein as "visual perception" or "perception".

The processing device 12 is further operative to process the received signals (collected nerve impulses) so as to generate (produce) digital image data that is representative of the perception (by the subject 40) of the visual stimuli. In other words, the generated digital image data is representative of what the subject 40 sees with his/her eyes 44 when the eyes 44 view (i.e., are exposed to) the visual stimuli.

In certain embodiments, the processing device 12 is further operative to process received digital image data, that is representative of a scene, to convert the image data into a sequence of nerve impulses, and to provide the nerve impulses to the visual cortex 43 such that the subject 40 visually perceives the scene as if the subject 40 had viewed the scene with his/her eyes 44. In certain embodiments, the processing device 12 provides the nerve impulses to the visual cortex 43 via the nerves 46 by inducing nerve transmission of the nerve impulses. In certain embodiments, the processing device 12 converts the image data to signals (e.g., electrical signals) that correspond to nerve impulses, and provides the nerve impulses to the nerves 46 by sending the converted signals to a microdevice, for example one or more microelectrodes or microtransducers, implanted in the subject 40 (e.g., at or on a portion of the nerves 46 or brain 42) that induces transmission of nerve impulses corresponding to the converted signals.

As will be discussed in further detail below, the image data that is to be received and processed by the processing device 12 for conversion to nerve impulses can be image data captured by an imaging device (e.g., camera) 28 electrically associated with the processing device 12, or can be image data retrieved from a computerized storage (i.e., memory) linked to, connected to, or otherwise associated with, the processing device 12.

With continued reference to FIG. 1, the communicative coupling of the processing device 12 to the visual cortex 43 can be effectuated by a machine-subject interfacing arrangement 18 (referred to hereinafter interchangeably as "interface") that places the processing device 12 in communication with the visual cortex 43 of the brain 42. In certain embodiments, the interface 18 can include two interfacing portions, namely a first interfacing portion 18a and a second interfacing portion 18b. The first interfacing portion 18a, also referred to as electronics interfacing portion 18a, is connected to the processing device 12. The second interfacing portion 18b, also referred to as a subject interfacing portion 18b, can be connected or coupled to the visual cortex 43 of the brain 42. The two portions 18a, 18b are interconnected via a linking portion 20 which in certain embodiments can provide a wired connection between the two portions 18a, 18b, and in other embodiments can provide a wireless connection between the two portions 18a, 18b.

Various deployment configurations for achieving communicative coupling of the processing device 12 to the visual cortex 43 are contemplated herein, and several of these deployment configurations will be described in further detail below. The deployment configurations described herein require some type of surgical implantation, which can employ invasive or semi-invasive techniques. For example, invasive techniques can include implantation by surgically accessing the subject's optic nerve and/or visual cortex through the subject's skull (i.e., surgically opening the skull). Surgeries performed on the brain, in particular the visual cortex and the optic nerve, have become common over the years, and it is asserted that a trained human surgeon and/or a robotic surgeon (such as used by the Neuralink Corporation of San Francisco, USA) can perform the necessary implantation. Semi-invasive techniques can include, for example, implantation by accessing the optic nerves or the optic chiasm through the nasal passageway via the sphenoid sinus. Before describing several deployment configurations, it is noted that the deployment configurations described herein are exemplary only and represent only a non-exhaustive subset of possible deployment options for the processing device 12. Other deployment options may be possible, as will be apparent to those of skill in the art.

In one example deployment configuration according to certain non-limiting embodiments, the processing device 12 communicates with the optic nerves 46 by tapping the optic nerves 46 via the interface 18. In such a deployment configuration, the subject interfacing portion 18b can be surgically implanted at or on a segment (section, portion) of the optic nerves 46, which in certain non-limiting implementations can be effectuated by first surgically cutting the optic nerves 46 to produce cut ends of the optic nerves 46, and then connecting the subject interfacing portion 18b to the cut ends. In such a deployment configuration, the processing device 12 preferably remains external to the brain 42 of the subject 40. When the processing device 12 is external to the subject 40, the subject interfacing portion 18b is surgically implanted at or on the optic nerves 46 together with either the entirety of the linking portion 20, or a segment of the linking portion 20 that connects to the subject interfacing portion 18b. If only the segment of the linking portion 20 that connects to the subject interfacing portion 18b is surgically implanted, the remaining segment of the linking portion 20, which connects to the electronics interfacing portion 18a, is external to the subject 40. Preferably, the segment of the optic nerves 46 at or on which the subject interfacing portion 18b is surgically implanted is the optic chiasm 48, which is the portion of the brain 42 at which the optic nerves 46 cross each other.

In another example deployment configuration, the processing device 12 is deployed external to the subject, and the subject interfacing portion 18b is surgically implanted at or on the visual cortex 43 together with either the entirety of the linking portion 20 or a segment of the linking portion 20 that connects to the subject interfacing portion 18b. If only the segment of the linking portion 20 that connects to the subject interfacing portion 18b is surgically implanted, the remaining segment of the linking portion 20, which connects to the electronics interfacing portion 18a, is external to the subject 40. Such an example deployment configuration is schematically illustrated in FIG. 1.

In yet another example deployment configuration according to certain non-limiting embodiments, the processing device 12 itself, together with the entirety of the interface 18, can be surgically implanted at or on the visual cortex 43. In another example deployment configuration according to non-limiting embodiments, the processing device 12 is surgically implanted at or on a segment of the optic nerves 46. FIG. 2 schematically illustrates such deployment configuration. Here, the surgical implantation can be effectuated, for example, by first surgically cutting the optic nerves 46 to produce cut ends 50a, 50b of the optic nerves 46, and then deploying the processing device 12 at the sight of the surgical cut and connecting the cut ends 50a, 50b of the optic nerves 46 to the processing device 12 via interface 18. In such a deployment configuration, the segment of the optic nerves 46 at or on which the processing device 12 is implanted is preferably, but not necessarily, the optic chiasm 48, whereby the optic nerves 46 are surgically cut (to produce cut ends 50a, 50b) at the optic chiasm 48. It is noted that in embodiments in which the processing device 12 or the interface 18 is surgically implanted at the optic nerve 46, care should be taken to ensure that the cut ends 50a, 50b, to which the processing device 12 is interfaced, correspond to the same nerve.

As mentioned above, the processing device 12 functions to process received signals that correspond to nerve impulses that are transmitted by one or more of the nerves 46 in response to one or more visual stimuli provided to one or both of the eyes 44 of the subject 40. The received signals can be the nerve impulses themselves, or can be signals which are produced (i.e., generated) in response to measurement or sampling of the nerve impulses by some microdevice, for example having microelectrodes or microtransducers, associated with the processing device 12. The processing device 12 processes the signals (collected nerve impulses) by applying a mapping function or functions to the signals. The mapping function maps between nerve impulses and digital image data, i.e., provides a transformation from nerve impulses to digital image data and vice versa, such that the received signals (that are representative of nerve impulses) are converted (transformed) to digital image data as a result of the application of the mapping function by the processing device 12. This nerve impulse to digital image data mapping function is preferably a one-to-one mapping, and is referred to hereinafter interchangeably as an "impulse-image mapping". By a one-to-one mapping, it is meant that a single nerve impulse signal maps to a single image data signal, and vice versa. Various example methods for generating impulse-image mapping functions will be described in detail in subsequent sections of the present disclosure.

With continued reference to FIGS. 1 and 2, refer also to FIG. 3, which shows an example block diagram of the processing device 12 according to a non-limiting embodiment of the present invention. The processing device 12 includes one or more processors 14 coupled to a computerized storage medium 16, such as a computerized memory or the like. The one or more processors 14 can be implemented as any number of computerized processors, including, but not limited to, microprocessors, microcontrollers, application-specific integrated circuits (ASICs), field programmable gate arrays (FPGAs), digital signal processors (DSPs), field-programmable logic arrays (FPLAs), and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel, as well as any combinations thereof. Implementation of the one or more processors 14 as quantum computer processors is also contemplated herein. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. It is noted that above-mentioned implementations of the one or more processors 14 represent a non-exhaustive list of example implementations. It should be apparent to those of ordinary skill in the art that other implementations of the processing device are contemplated herein, and that processing technologies not described herein or not yet fully developed, including for example biological computing technologies, may be suitable for implementing any of the processing devices discussed herein.

The storage/memory 16 can be any conventional storage media, which although shown as a single component for representative purposes, may be multiple components. The storage/memory 16 can be implemented in various ways, including, for example, one or more volatile or non-volatile memory, a flash memory, a read-only memory, a random-access memory, and the like, or any combination thereof. In certain embodiments, the storage/memory 16 can include one or more components for storing and maintaining the impulse-image mapping, and at least one component configured to store machine executable instructions that can be executed by the one or more processors 16.

Figure 7:
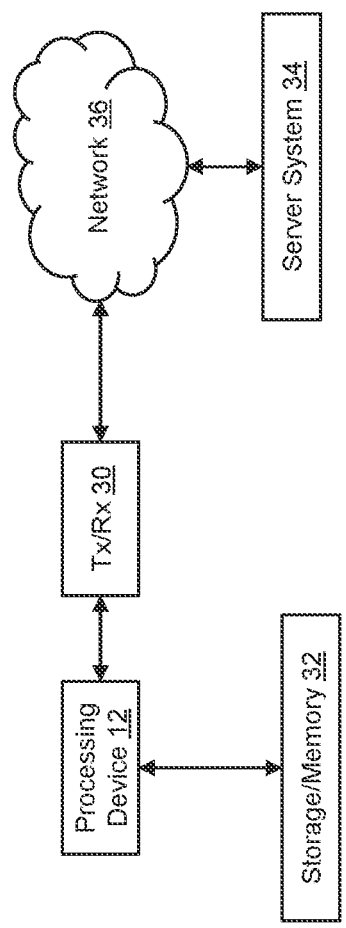
FIG. 7 is a schematic representation of a system environment in which the processing device according to embodiments of the invention can operate, showing a memory for storing data received from the processing device, and a transceiver unit connected to the processing device for exchanging data with a remote server via a communication network.

In certain embodiments, the processing device 12 is further operative to perform at least one operation on the generated image data (which includes the image data generated by the processing device 12 by processing nerve impulses via application of the impulse-image mapping) in accordance with one or more rules or handling criteria. For example, the processing device 12 can be configured to operate on the generated image data according to a set of data storage rules or criteria, such that the processing device 12 sends some or all of the generated digital image data to one or more computerized storage/memory devices associated with the processing device 12. Such associated storage/memory devices can include, for example, the storage/memory 16, or other storage/memory devices that are linked or connected to the processing device 12, such as, for example, an external storage/memory 32 or a server system 34 having a memory (FIG. 7).

In embodiments in which the processing device 12 sends some or all of the generated image data to a server system 34, the server system may be a remote server system, whereby the processing device 12 sends the image data to the server system 34 via a communication network 36 (which can be one or more communication networks, such as cellular networks, local area networks, the Internet, etc.). In such embodiments, the processing device 12 can be linked to a transceiver (Tx/Rx) unit 30 that provides a communication/network interface for transmitting/receiving data to/from (i.e., exchanging data with) the network 36.

In another non-limiting example, the processing device 12 can be configured to operate on the generated image data according to a set of data modification or manipulation rules or criteria. For example, the processing device 12 can modify the generated image data by deleting certain segments (e.g., pixels) of the image data, and/or changing certain elements of the image data, for example changing pixel values in the image data to modify one or more of the color, contrast, shape, or other features of the image data, and/or augmenting the image data by appending additional image data to, or incorporating additional image data into, the generated image data. The modified image data can also be stored in memory (e.g., storage/memory 16 and/or external storage/memory 32 and/or server system 34).

In certain embodiments, the processing device 12 is further operative to convert digital image data to nerve impulses (or electrical signals that represent nerve impulses) to be transmitted by the nerves 46. The conversion of image data to nerve impulses is effectuated by applying the impulse-image mapping function discussed above. The image data that is to be converted to nerve impulses can be, for example: i) image data obtained from an external source, such as an imaging device that generates image data, or a memory that stores image data, ii) image data generated from collected nerve impulses, iii) the modified image data resultant from the modification applied by the processing device 12 discussed above, or iv) some combination of i), ii) and iii).

The image data provided to the processing device 12 can be in any suitable image or video format or standard, including, for example, JPG, PNG, GIF, TIF, AVI, MPEG, etc. Furthermore, the image data can be transmitted or sent to the processing device 12 using any suitable image/video transmission format or standard, including, for example, RTSP, TCP, UDP, and the like, as well as any other commonly used standards for data transmission, including wireless data transmission standards such as cellular standards (e.g., 3G, 4G/LTE, 5G, etc.), wireless communication standards (e.g., Wi-Fi, Bluetooth, etc.) and the like, and wired communication standards.

In another non-limiting example, the processing device 12 can be configured to operate on the generated image data according to a set of display rules or criteria. For example, the processing device 12 can be configured to provide the generated digital image data to a display device connected or linked to the processing device 12 such that the display device displays images or video represented by the digital image data. The processing device 12 can transmit or send the digital image data to such a display device using any suitable image/video transmission format or standard, or any commonly used standards for data transmission, including any of the formats and standards discussed above.

In the exemplary embodiments illustrated in FIGS. 1 and 2, the system 10 further includes imaging device 28 (referred to interchangeably herein as camera 28) that is operative to capture images (which can include video) of a scene. In certain embodiments, the imaging device 28 can be used as bionic/electronic eyes of the subject 40 for allowing the subject 40 to view the scene captured by the imaging device 28 or for augmenting the subject's natural view of an environment with scene images captured by the imaging device 28. The imaging device 28 is further operative to send the captured images to the processing device 12 as image data. The image data in the images captured by the imaging device 28 can be provided in any suitable image or video format or standard, including any of the standards discussed above. Furthermore, the imaging device 28 can transmit the captured images/video to the processing device 12 using any suitable image/video transmission format or standard, or any commonly used standards for data transmission, including any of the formats and standards discussed above.

With continued reference to FIGS. 1-3, refer also to FIG. 4, which illustrates a non-limiting deployment configuration of the imaging device 28. Here, the imaging device 28 is mounted to a subject 40 positioned in an environment that includes a scene 52. The imaging device 28 is mounted to the subject 40 such that the scene or section of the environment to be imaged by the imaging device 28 is within the field of view (FOV) of the imaging device 28. In the example deployment configuration illustrated in FIG. 4, the imaging device 28 is mounted to the head of the subject 40, for example via strap or band 54, as a forward-facing camera so as to capture images of the scene in front of the subject 40. However, the imaging device 28 can be deployed in other ways, for example as a rear-facing camera deployed to capture images of the scene behind the subject. Furthermore, the imaging device 28 can be deployed as a non-head-mounted device, for example as being hand-carried by the subject, or mounted to another portion of the subject's body, such as portions of the torso (chest, mid-section, waist), arms, legs, and the like.

Although illustrated as a single device, the imaging device 28 can include multiple cameras, where each camera is deployed to image the same regions of the scene or different regions of the scene. For example, one camera can be deployed to capture images of a first region of a scene, and another camera can be deployed to capture images of a second region of the scene that is different from the first region. For example, one camera can be deployed as a forward-facing camera that images regions of the scene in front of the subject, and another camera can be deployed a rear-facing camera that images regions of the scene behind the subject. In another example, both cameras can be deployed to capture images of the same region or overlapping regions of the scene, for example, a pair of forward-facing cameras having the same FOV or overlapping FOV can be deployed, or a pair of rearward-facing cameras having the same FOV or overlapping FOV can be deployed.

In other deployment configurations, the imaging device 28 can be remote from the subject 40, for example the subject 40 can be positioned in an environment in a first geographic location, and the imaging device 28 can be located in a second geographic location that is remote from the first geographic location. In such configurations, the imaging device 28 preferably includes or is connected to a transceiver device that is operative to transmit the image data captured by the imaging device 28 to a transceiver (e.g., Tx/Rx unit 30 of FIG. 7) connected to the processing device 12 via one or more communication networks.

In certain embodiments, the imaging device 28 can be used together with the processing device 12 to provide electronic eyes to the subject. The subject can keep their eyes closed while the imaging device 28 captures images from a scene (which can be the same scene the subject would see with open eyes, or can be a different scene). The images captured by the imaging device 28 are sent to the processing device 12 as image data, which converts the image data to nerve impulse signals using the impulse-image mapping. The processing device 12 then transmits the nerve impulses to the brain 42 via the optic nerves 46, where the brain 42 the interprets the received nerve impulses as sight/vision such that the subject visually perceives the images captured by the camera 28 as if the subject were viewing the scene with open eyes. In other embodiments, digital image data stored in memory associated with the processing device 12 (e.g., storage/memory 16 and/or external storage/memory 32 and/or server system 34) can be uploaded to the processing device 12. The processing device 12 can process the uploaded image data using the impulse-image mapping in order to convert the image data to nerve impulses. The processing device 12 can then transmit the nerve impulses to the brain 42 such that the nerve impulses are interpreted by the brain 42 as sight/vision. For example, a series of images, such as a movie, can be stored in such a memory, and uploaded/streamed to the subject.

According to certain embodiments of the present invention, the system 10 can be used to provide a mixed-reality experience to the subject 40 by fusing a scene image (or images) with one or more additional images. In one set of non-limiting examples, the fusing can be performed when the subject 40 is viewing a real-world scene with his/her eyes 44. In a first example, the fusing can be accomplished by using the processing device 12 to convert nerve impulses, generated by the subject 40 in response to viewing the real-world scene, to digital image data. The processing device 12 can then modify the digital image data to include parts of image data generated by the camera 28 when capturing images of the scene. The processing device 12 can then convert the modified image data to nerve impulses and provide those nerve impulses to the visual cortex, such that the subject perceives the viewed scene and the parts of the camera image as a single image. In a second example, the fusing can be accomplished by using the processing device 12 to convert digital image data (obtained, for example, from the camera 28 or a computer memory device) to nerve impulses (or electrical signals representative of nerve impulses), and to provide those nerve impulses to the optic nerves 46 such that the nerve impulses are transmitted to the visual cortex 43 of the brain 42. The brain 42 then combines the image information (carried by the nerve impulses generated by the processing device 12) with the image information (carried by the nerve impulses generated by the subject 40 in response to viewing the real-world scene) as a single image.

In another non-limiting example, the camera 28 can be used to capture an image of a scene, and the processing device 12 can modify the image data (generated by the camera 28) to include additional image data representative of a different image. The processing device 12 can combine this modified image with image data generated from nerve impulse (generated by the subject 40 in response to viewing the real-world scene) and then convert the combined image data to nerve impulses and provide those nerve impulses to the brain 42 (for example via the optic nerves 46), whereupon the brain 42 interprets the nerve impulses (which carry image information corresponding to the scene image and the different image) as a single image.

Parenthetically, it is noted herein that the nerve impulses which are converted, by the processing device 12, from digital image data should be provided to the visual cortex of the subject at an appropriate rate so that the subject can perceive the corresponding image data. Specifically, if the nerve impulses are provided to the visual cortex too quickly, the subject will not be able to perceive the corresponding image (i.e., the images will change too quickly for the subject to notice, which may become disorienting to the subject). Likewise, if the nerve impulses are provided to the visual cortex too slowly, the subject may perceive a corresponding image that is no longer relevant to the real-world scene that the subject is viewing with his/her eyes. Thus, the processing device 12 preferably controls the timing at which any such nerve impulses are provided to the visual cortex 43, to ensure that the subject is able to appropriately perceive the corresponding image. The rate at which the nerve impulses (converted from image data) are provided to the visual cortex may be user (i.e., subject) specific, since some users may be able to perceive images at a faster or slower rate than other users. Thus, the control of the timing (rate) at which nerve impulses are provided to the visual cortex is preferably adjustable by the user of the system 10.

In the electronic eye and/or the mixed-reality embodiments described above, the processing device 12 may be further operative to convert the nerve impulses to digital image data and to perform at least one operation on the digital image data according to one or more rules or criteria. For example, the processing device 12 can be configured to operate on the digital image data according to a set of data storage rules or criteria, and/or be configured to operate on the digital image data according to a set of data modification or manipulation rules or criteria, similar to as discussed above.

It is noted herein that the processing device 12 can employ various techniques for obtaining nerve impulses (and their representative electrical signals) from the nerves 46 of the subject and for providing nerve impulses (converted from digital image data) to the nerves 46 to induce transmission (by the nerves 46) of the provided nerve impulses. Such techniques may typically rely on employing microdevices, such as microelectrodes or microtransducers, for measuring (receiving) nerve impulses and producing electrical signals in response thereto, and/or for stimulating the nerves 46 with electrical signals so as to induce transmission of the corresponding nerve impulses. Various entities have conducted research, development, and experimentation on connection and interfacing of computer processing devices to the brain, tissue, and nerves via implantation or other invasive or semi-invasive means. One example of such research can be found in a publication by the University of Luxembourg in 2019 entitled "CONNECT—Developing nervous system-on-a-chip" (available at haps://wwwfr.uni.lu/lcsb/research/developmental_and_cellular_biology/news/connect developing_nervous_system_on_a_chip), which describes culturing individual nervous system components and connecting the components in a microfluid chip (integrated circuit).

Examples of research and experimentation in the field of brain-machine interfacing is described in an article published in Procedia Computer Science in 2011, entitled "Brain-Chip Interfaces: The Present and The Future" by Stefano Vassanelli at the NeuroChip Laboratory of the University of Padova in Italy. In one example, computerized processing devices are interfaced to neurons with metal microelectrodes or oxide-insulated electrical microtransducers (e.g., electrolyte-oxide-semiconductor field-effect transistors (EOSFETs) or Electrolyte-Oxide-Semiconductor-Capacitors (EOSCs)) to record (i.e., measure) or stimulate neuron electrical activity. In another example, large-scale high-resolution recordings (i.e., measurements) from individual neurons are obtained using a processing device that either employs or is coupled to a microchip featuring a large Multi-Transistor-Array (MTA). In yet a further example, a microchip featuring a large MTA is used to interface with the cells in vitro by deploying the MTA in contact with brain tissue, where the signals corresponding to nerve impulses are, in one example, in the form of local-field-potentials (LFPs).

An example of a brain-machine interface device is the Neuralink device, developed by Neuralink Corporation of San Francisco, USA. The Neuralink device includes an ASIC that digitizes information obtained from neurons via microelectrodes.

Bearing the above in mind, the following paragraphs provide a high-level description of an interface 18 that can be used for connecting/interfacing the processing device 12 to the subject 40 so as to provide a machine-brain interface, according to non-limiting example embodiments of the present invention.

With continued reference to FIGS. 1-4, refer also to FIG. 5, which illustrates a schematic representation of the interface 18 according to a non-limiting embodiment of the invention. Here, the subject interfacing portion 18b includes an electrode array 22, having a plurality of electrodes 23, that is deployed at or on the optic nerves 46 (e.g., at or on the optic chiasm 48). The electrodes 23 are preferably microelectrodes, such as EOSFETs or EOSCs. In embodiments in which the processing device 12 is operative to convert nerve impulses to digital image data, the electrode array 22 is operative to measure nerve impulses transmitted by the optic nerves 46 and produce (in response to the measurements) electrical signals associated with (and representative of) the nerve impulses, and provide those signals to the processing device 12 in order to enable the processing device to collect the nerve impulses and process the electrical signals that correspond to (i.e., represent) the nerve impulses. In the illustrated embodiment, the linking portion 20 can be implemented as a wire or cable that provides a physical transmission medium along which the electrical signal can propagate to the processing device 12. In certain embodiments, the interface 18 can employ a transducer (preferably a microtransducer as discussed above) as part of the subject interfacing portion 18b, either instead of or in addition to electrode array 22. The transducer can be used together with the processing device 12 for conversion of nerve impulses to digital image data. For example, the transducer can generate electrical signals in response to receiving (measuring) nerve impulses transmitted by the optic nerves 46. The generated electrical signals correspond to (i.e., are representative of) the nerve impulses, and are provided to the processing device 12 for processing using the impulse-image mapping.

In embodiments in which the processing device 12 is operative to convert the image data to nerve impulses and transmit the nerve impulses to the brain 42 via the optic nerves 46 such that the nerve impulses are interpreted by the brain 42 as sight/vision, the transmission of the nerve impulses can be effectuated by stimulation of one or more neurons of the optic nerves 46 by a microdevice, e.g., the electrode array 22 (or a transducer). Generally speaking, in such embodiments the processing device 12 can convert (using the impulse-image mapping) image data to nerve impulses (or electrical signals that represent nerve impulses) that are to be transmitted by the nerves 46. The processing device 12 then provides the nerve impulses to the nerves 46 to induce nerve transmission of the nerve impulses (or provides the electrical impulses to the nerves 46 to induce nerve transmission of the nerve impulses represented by the electrical impulses). In certain embodiments, the inducing of nerve transmission can be effectuated by the processing device 12 providing electrical signals to the electrode array 22 (or a transducer), which stimulates the neurons of the optic nerves 46 in accordance with the electrical signals so as to induce transmission of corresponding nerve impulses.

Figure 6:
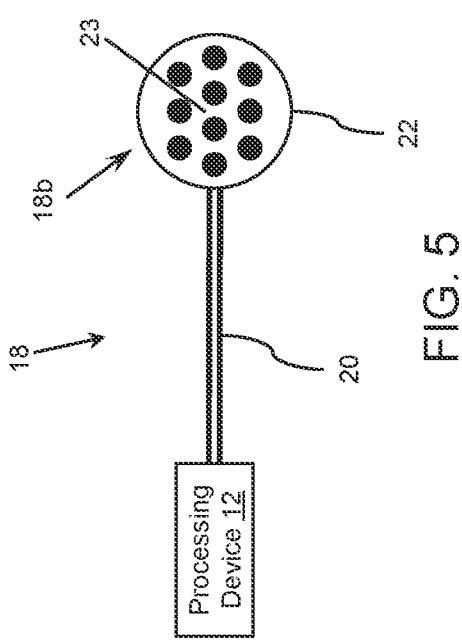
FIG. 6 is a schematic representation of an exemplary wireless interface that can be used for interfacing between the processing device and the visual cortex of the subject, showing a transmitter unit connected to the processing device, and an electrode array connected to a receiver unit, according to an embodiment of the present invention.

FIG. 6 illustrates another embodiment that employs wireless signal transmission for providing electrical signals to the microdevice, represented here as electrode array 22. Here, the processing device 12 is connected to a transmitter (Tx) unit 24 via a wire or cable 25, and the electrode array 22 is connected to a receiver (Rx) unit 26 via a wire or cable 27. The Tx unit 24 includes transmitter circuitry and components (e.g., signal transmission electronics, one or more antenna, etc.) for transmitting the electrical signals produced by the processing device 12 via a wireless interface to the Rx unit 26. The Rx unit 26 includes one or more antennas which receive the electrical signals, and provide the received signals to the electrode array 22 which stimulate the nerves 46 to induce the nerves 46 to transmit nerve impulses corresponding to the electrical signals.

It is noted that in certain embodiments, the interfacing arrangement 18 can include multiple interfaces. For example, a first interface can be used to effectuate conversion of image data to nerve impulses. The first interface can employ an electrode array 22 or microtransducers (implemented, for example, as EOSCs) connected or linked to the processing device 12 via a wired connection (for example as shown in FIG. 5) or wireless connection (for example as shown in FIG. 6). A second interface can be used to effectuate conversion of nerve impulses to image data. The second interface can employ an electrode array 22 and/or microtransducers (implemented, for example, as EOSFETs) connected or linked to the processing device 12 via a wired connection (for example as shown in FIG. 5).

The following paragraphs describe various methods and techniques for generating impulse-image mapping functions, as well as exemplary processes for applying the mapping functions. By employing an impulse-image mapping, the system 10 according to embodiments of the present invention can convert images perceived by the eyes 44 (i.e., vision) into digital image data, and can convert digital image data (obtained from computer images, image sensors, cameras, and the like) into nerve impulses that can be routed to the brain to induce visual perception and/or augment vision.

According to certain embodiments, generation of the impulse-image mapping can be aided by machine learning (ML) or neural networks (NN) algorithms. For example, the processing device 12 can employ one or more ML or NN algorithms to learn the signal format of nerve impulses (in response to visual stimuli provided to the eyes 44), and to determine the mapping by comparing the nerve impulse format to digital images stored in a memory associated with the processing device 12. In certain embodiments, the stored digital images can be generated by the imaging device 28.

As part of one non-limiting example process for generating the impulse-image mapping, a sample picture/image can be positioned in front of the eyes 44 as a visual stimulus such that the light from the sample is collected (captured) by the eyes 44 and the processing device 12 collects the nerve impulses sent from the eyes 44 to the brain 42 (along the optic nerves 46) in response to the subject viewing the sample. A digital image having image data representative of the same sample can also be stored in a memory associated with the processing device 12 (e.g., storage/memory 16). The digital image can be generated, for example, by the imaging device 28. The resolution of the digital image is preferably in accordance with a standard resolution, such as, for example, 1920 pixels by 1080 pixels, 1280 pixels by 960 pixels, 800 pixels by 600 pixels, etc. Subsequently, a small change can be made to the sample image, for example by changing a single pixel of the sample image, to produce a new sample image. The new sample image is then placed in front of the eyes 44, and the processing device 12 collects the nerve impulses sent from the eyes 44 to the brain 42 in response to viewing the new sample image. A digital version of the new sample image, i.e., a digital image having digital image data representative of the new sample, is also preferably stored in the memory (e.g., storage/memory 16) associated with the processing device 12. The digital version of the new sample image can be generated by the processing device 12 applying changes to the pixel in the original digital image. This process can continue by making incrementally larger changes to the sample image (e.g., changing two pixels, then changing five pixels, then changing 10 pixels, etc.). For each changed pixel, the change in the nerve impulse from the eyes 44 (compared to the previous sample) is compared with the change between the new digital image data and the previous digital image data. This process can continue using several different sample images, until each nerve impulse from the eye 44 can be matched in a one-to-one fashion to a corresponding image pixel. This matching between each nerve impulse and a corresponding image pixel constitutes a mapping between nerve impulses and images (i.e., an impulse-image mapping).

In certain embodiments, the mapping function is stored as, or together with, a configuration table that maintains nerve-impulse-to-image and image-to-nerve-impulse conversion parameters. The configuration table includes all of the image attributes/features, including color, intensity, position, and a nerve impulse encoding value. The size of the table may be in accordance with the resolution of the image, such that for each pixel (or group of pixels), the image data of that pixel (or group of pixels) has a corresponding value for color, intensity, position, and nerve impulse code.

In a preferred but non-limiting implementation of the process for generating the mapping, anchor points or regions of the digital image are processed first. The anchor points include a pixel (or a group of pixels, typically made up of at least four pixels) at each of the four corners of the digital image, as well as a pixel (or group of pixels) at the center of each edge (i.e., top, bottom, left, and right) of the digital image, resulting in eight anchor points. The color and intensity of each of the eight pixels are correlated with the corresponding nerve impulses when the corresponding anchor points in the sample picture (based on the determined position of the anchor points) are viewed by the eye 44. When groups of pixels are used, the average color and intensity of the pixels in each group is calculated and set as the color and intensity of the pixel group.

The color and intensity values for the pixels are stored in a table, together with the values of the registered corresponding nerve impulses. Some or all of the pixel values for the anchor points are then changed, and the sample image displayed to the eye 44 is correspondingly changed, and the color and intensity of each of the eight pixels are correlated with the corresponding nerve impulses when the corresponding anchor points in the sample picture are viewed by the eye 44. This process can be repeated several times, until the correlation between the pixels of the anchor points (either individual pixels or groups of pixels) and the corresponding nerve impulses is verified. The mapping function generation process can then proceed to changing the color and intensity values of selected pixels or groups of pixels that are non-anchor pixels. The changes can be made according to a particular pre-defined sequence, which can include the sequence of color and intensity values for the selected pixels, and then the sequence of selected pixels. In this way, a pixel or group of pixels is selected (according to a pixel selection sequence), and the color and intensity values of the selected pixel(s) are changed according to a color/intensity sequence, and then another pixel or group of pixels is selected (according to the pixel selection sequence) and the color and intensity values of the selected pixel(s) are changed according to the color/intensity sequence, and so on and so forth, until all combinations of color/intensity values across all pixels have been implemented and the corresponding nerve impulses have been recorded/stored (in the table).

Parenthetically, after each pixel or group of pixels is selected and the color/intensity values have been incrementally changed to produce a correlation between nerve impulses and the color/intensity values for those pixels, the accuracy of the correlation can optionally be checked by converting nerve impulses to digital image data using the partial table having the color/intensity values for the selected pixels.

The full table can then be used to convert nerve impulses (collected in response to the eye 44 viewing a sample picture) to a digital image to produce a generated digital image. The generated digital image is then compared to a digital image stored in the memory (e.g., storage/memory 16) associated with the processing device 12 (which in certain embodiments can be generated by the camera 28 in response to capturing an image of the sample picture). The comparison can be performed on a pixel-by-pixel basis. If the comparison yields a pixel matching that is within a preferred accuracy level (e.g., if 90% of the pixels of two images are the same), the mapping process is complete. If the comparison does not yield a pixel matching that is within the preferred accuracy level, the correlation process can be repeated, i.e., anchor points can be selected and the color/intensity values of the pixels can be incrementally changed.

In operation, when converting from image digital data to nerve impulses, the processing device 12 can operate on the pixels of the digital image data either serially or in parallel. For example, the processing device 12 can read the digital image pixel-by-pixel and line-by-line. When performing serial conversion, the processing device 12 can read each pixel and then convert that pixel to a corresponding nerve impulse before the next pixel is read and converted. When performing parallel conversion, for example, the pixels can be read one at a time and then groups of the read-in pixel can be converted to corresponding nerve impulses (in certain cases, all of the pixels can be converted at once, i.e., as a single group).

When converting from nerve impulses to digital image data, the processing device 12 may, in certain processing architectures, operate on the received nerve impulses in a first-in-first-out manner so as to generate pixel data one pixel at a time. In other processing architectures, the processing device 12 may operate on groups of received nerve impulses in parallel, for example by storing the data representative of the signals that correspond to the nerve impulses in the group in temporary memory, and then operating on the stored data in parallel so as to produce corresponding pixel data.

Referring now again to FIG. 1, in preferred embodiments the system 10 also includes a control unit 15 that is connected or linked (electronically) to the processing device 12 and the camera 28, and is configured to control the operation of the camera 28 and the processing device 12. The control unit 15 preferably includes one or more user input interfaces (e.g., touchscreen, pushbuttons, dials, knobs, electronics keypad, (electronic) keyboard, etc.) that allow the user to provide input to the control unit 15. In response to receiving input via the user input interface, the control unit 15 is preferably operative to provide control commands to the processing device 12 and/or the camera 28 which control or change the operation of the processing device 12 and/or the camera 28.

In one example, the control unit 15 allows the user to define the rules or handling criteria that determine the at least one operation performed on generated image data by the processing device 12, as well as to select the handling rule and/or change from the selected rule to another rule. For example, the user can select data storage rules, data modification rules, or display rules, such that the processing device 12 operates according to a set of data storage rules (criteria), a set of data modification (manipulation) rules, or a set of display rules (criteria), respectively. In addition, the user can select, via the control unit 15, parameters related to the defined rules. For example, if the user selects that the processing device 12 is to operate according to a set of data modification (manipulation) rules, the user can select how the generated digital image data is to be modified, including selecting any image data that is to be used to modify generated digital image data. As another example, if the user selects that the processing device 12 is to operate according to a set of data storage rules, the user can select the memory device (e.g., storage/memory 16, external storage/memory 32, server system 34) for storing generated image data, as well as select which portions of the generated image data are to be stored on which memory device (e.g., some of the generated image data can be stored locally in storage/memory 16, whereas other parts of the generated image data can be stored remotely at server system 34).

The control unit 15 also preferably allows the user to select image data that is to be converted to nerve impulses by the processing device 12. The selection can be applied via a menu that is part of the user input interface of the control unit 15. In addition, the control unit 15 preferably allows the user to adjust and set the rate at which nerve impulses, converted from digital image data by the processing device 12, are provided to the visual cortex. The rate setting can be applied via the user input interface of the control unit 15.

In certain preferred embodiments, the control unit 15 provides selective switching between different operational modes of the system 10 in response to user input. For example, the control unit 15 can selectively switch the camera 28 on or off, and/or actuate the camera 28 to capture images of a scene, and/or actuate the processing device 12 to retrieve image data from the camera 28 or a memory (e.g., storage/memory 16, storage/memory 32, a server system 34). As such, the control unit 15 can enable the user to control if and when images (digital image data) from a memory (e.g., storage/memory 16, storage/memory 32, a server system 34) or captured by the camera 28 are converted to nerve impulses, and/or if and when the nerves 46 are induced to transmit such converted nerve impulses. In this way, the user can control if and when the user perceives digital images, akin to selectively switching electronic/bionic eyes on and off.

In addition, the control unit 15 is preferably operative to actuate the processing device 12 to adjust image parameters (including the color and intensity of individual pixels or groups of pixels) of captured images that are stored in a memory associated with the processing device 12, and/or adjust image parameters of digital image data that are to be converted to nerve impulses. For example, the image format of digital image data that is stored in memory or received from camera 28, and that is to be uploaded to the visual cortex post nerve impulse conversion, may be full color format. However, the user may wish to view the image data in black and white image format, and can employ the control unit 15 to actuate the processing device 12 to convert the full color image to a black and white image, such that the uploaded image data that is to be converted to nerve impulses is a black and white image.

The control unit 15 is a computerized control unit that includes one or more computer processors coupled to a computerized storage medium (e.g., memory). The one or more processors can be implemented as any number of computerized processors, including, but not limited to, as microprocessors, microcontrollers, ASICs, FPGAs, DSPs, FPLAs, state machines, and the like. In microprocessor implementations, the microprocessors can be, for example, conventional processors, such as those used in servers, computers, and other computerized devices. For example, the microprocessors may include x86 Processors from AMD and Intel, Xeon® and Pentium® processors from Intel. The aforementioned computerized processors include, or may be in electronic communication with computer readable media, which stores program code or instruction sets that, when executed by the computerized processor, cause the computerized processor to perform actions. Types of computer readable media include, but are not limited to, electronic, optical, magnetic, or other storage or transmission devices capable of providing a computerized processor with computer readable instructions. The storage/memory of the control unit 15 can be any conventional storage media and can be implemented in various ways, including, for example, one or more volatile or non-volatile memory, a flash memory, a read-only memory, a random-access memory, and the like, or any combination thereof. In certain embodiments, the storage/memory of the control unit 15 can store machine executable instructions that can be executed by the one or more processors of the control unit 15.

In certain embodiments, the processing device 12 and the control unit 15 share one or more common processors, such that the processing device 12 is operative to perform both processing and control functionality. In other sometimes more preferable embodiments, the control unit 15 and the processing device 12 are separate electronic devices that are electronically connected via a wired or wireless connection. In such embodiments, the control unit 15 can be implemented as a user computer device, which includes, for example, mobile computing devices including but not limited to laptops, smartphones, and tablets, and stationary computing devices including but not limited to desktop computers.

Although the embodiments described thus far have pertained to using a single processing device 12 that is operative to convert nerve impulses, that are received in response to visual stimulation of the eye, to digital image data, and is further operative to convert digital image data to nerve impulses and to provide those nerve impulses to the visual cortex, other embodiments are possible in which the tasks of conversion of nerve impulses to digital image data and the conversion of digital image data to nerve impulses are subdivided amongst two (or more) processing devices 12. Such embodiments may be of particular value in situations in which a large segment of the optic nerves between the eye and the visual cortex has been cut or removed, for example as a result of a surgical procedure for treatment of a disease. For example, removal of cancerous tumors in the vicinity of the optic nerves may result in the removal of the majority of the optic nerves, which can lead to loss of vision. By utilizing two processing devices, the two processing devices can provide restored vision to a subject.

Figure 8:
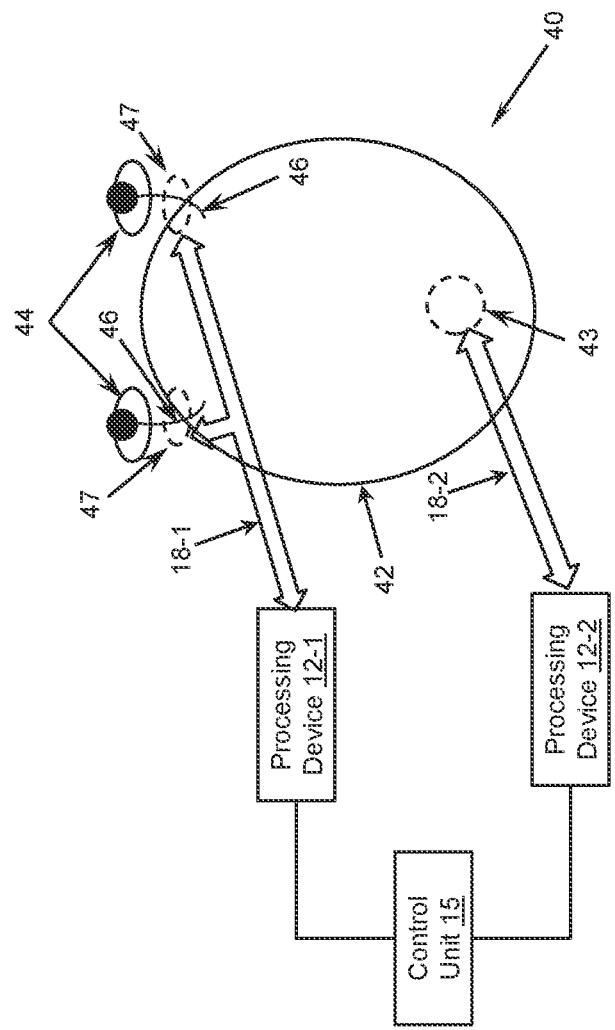
FIG. 8 is a schematic representation of a system similar to the system illustrated in FIG. 1 but in which a pair of processing devices interfacing with different respective parts of the subject are deployed, according to an embodiment of the present invention.

FIG. 8 schematically illustrates a non-limiting embodiment that utilizes first and second processing devices, labeled as processing devices 12-1, 12-2. In the illustrated embodiment, the optic nerves 46 have been severed such that a majority of the optic nerves that connect between the eyes and the visual cortex is missing. The processing devices 12-1, 12-2 in combination can, in certain embodiments, operate similar to the processing device 12 to act as a bridge between the eyes and the visual cortex (or optic nerve bypass) whereby nerve impulses generated in response to visual stimulation of the eyes 44 can reach the visual cortex 43 via the processing devices 12-1, 12-2.

The first processing device 12-1 is communicatively coupled to the optic nerves 46, via an interface 18-1 (which can be similar in structure and operation to any of the interfaces 18 described above), at a portion 47 of the optic nerves 46 that is in proximity to the eye 44 (e.g., at or near the optic canal). The first processing device 12-1 is operative to receive nerve impulses, generated in response to visual stimulation of the eye 44, that are to be transmitted to the visual cortex via the optic nerves 46, and convert those nerve impulses to digital image data (similar to as described above). In certain embodiments, the processing device 12-1 can obtain signals representative of the nerve impulses via the interface 18-1, which may include one or more EOSFETs at the subject interfacing portion of the interface 18-1 for measuring or sampling the nerve impulses and producing electrical signals in response thereto. The processing device 12-1 can then convert those signals to digital image data using the techniques discussed above.

The second processing device 12 can be communicatively coupled to the visual cortex 43, for example via surgical implantation of a subject interfacing portion of an interface 18-2 at or on the visual cortex 43, or via surgical implantation of the second processing device 12 at or on the visual cortex 43. The interface 18-2 can be similar in structure and operation to any of the interfaces 18 described above. The two processing devices 12-1, 12-2 are linked or connected to each other, for example indirectly via the control unit 15 as illustrated, or directly via any suitable data connection means (for example a data bus or the like). The second processing device 12-2 is operative to receive the digital image data generated by the first processing device 12-1, and to convert the received image data to nerve impulses, and to provide those nerve impulses to the visual cortex 43 (via the interface 18-2 according to any suitable technique including the techniques described above) such that the subject 40 perceives the image captured by the eyes 44. In certain embodiments, the processing device 12-2 converts the digital image data to electrical signals, and the processing device 12-2 provides those electrical signals to the subject interfacing portion of the interface 18-2, which may include one or more EOSCs, to stimulate the visual cortex 43 in accordance with the electrical signals.

Each of the processing devices 12-1 and 12-2 is similar in structure to the processing device 12 described above, i.e., each of the processing devices 12-1 and 12-2 includes one or more processors coupled to a computerized storage medium. In certain embodiments, either or both of the processing devices 12-1, 12-2 is further operative to modify digital image data in a manner similar to the data modification performed by the processing device 12 described above. For example, the first processing device 12-1 may modify the digital image data (converted from nerve impulses by the first processing device 12-1) and then send the modified image data to the second processing device 12-2. Alternatively or in addition to the first processing device 12-1 modifying the digital image data, the second processing device 12-2 may modify the digital image data received from the first processing device 12-2, and then convert the modified digital image data to nerve impulses.

In certain embodiments, either or both of the processing devices 12-1, 12-2 can be linked to an external storage/memory (similar to external storage/memory 32 in FIG. 7). In other embodiments, either or both of the processing devices 12-1, 12-2 can include or be linked to a Tx/Rx unit, similar to the Tx/Rx unit 30 in FIG. 7, that provides a communication/network interface for transmitting/receiving data to/from (i.e., exchanging data with) a communication network. In such embodiments, either or both of the processing devices 12-1, 12-2 can communicate (i.e., exchange data) with a remote server system (such as server system 34) via the communication network.

Although the embodiments of the present invention are of particular use when applied within the context of human vision, embodiments of the present disclosure may be equally applicable to vision in non-human animal subjects, including, but not limited to, other primate species (e.g., monkeys, gorillas, etc.), canine species, feline species, etc. In such non-human applications, nerve impulses can be collected via the same or similar interfacing methods discussed above, and converted to digital images by the processing device 12 using a species-specific impulse-image mapping. Since different species have photoreceptor cells that are sensitive to different wavelengths of light, some species can perceive colors that other species cannot perceive.

The resultant digital image data can, for example, be output to another system for further processing or use. For example, the digital image data generated from nerve impulses in a canine subject can be provided for display to be viewed by a human subject, or can be converted to nerve impulses using a human impulse-image mapping function and provided to the optic nerves of a human subject.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, non-transitory storage media such as a magnetic hard-disk and/or removable media, for storing instructions and/or data. Optionally, a network connection is provided as well. A display and/or a user input device such as a keyboard or mouse are optionally provided as well.

For example, any combination of one or more non-transitory computer readable (storage) medium(s) may be utilized in accordance with the above-listed embodiments of the present invention. The non-transitory computer readable (storage) medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

As will be understood with reference to the paragraphs and the referenced drawings, provided above, various embodiments of computer-implemented methods are provided herein, some of which can be performed by various embodiments of apparatuses and systems described herein and some of which can be performed according to instructions stored in non-transitory computer-readable storage media described herein. Still, some embodiments of computer-implemented methods provided herein can be performed by other apparatuses or systems and can be performed according to instructions stored in computer-readable storage media other than that described herein, as will become apparent to those having skill in the art with reference to the embodiments described herein. Any reference to systems and computer-readable storage media with respect to the following computer-implemented methods is provided for explanatory purposes, and is not intended to limit any of such systems and any of such non-transitory computer-readable storage media with regard to embodiments of computer-implemented methods described above. Likewise, any reference to the following computer-implemented methods with respect to systems and computer-readable storage media is provided for explanatory purposes, and is not intended to limit any of such computer-implemented methods disclosed herein.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As used herein, the singular form "a", "an" and "the" include plural references unless the context clearly dictates otherwise. For example, reference to a single nerve can also refer to both nerves of a nerve pair. Furthermore, reference to both nerves of a nerve pair can also refer to a single nerve, unless the context clearly dictates otherwise.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The above-described processes including portions thereof can be performed by software, hardware and combinations thereof. These processes and portions thereof can be performed by computers, computer-type devices, workstations, processors, micro-processors, other electronic searching tools and memory and other non-transitory storage-type devices associated therewith. The processes and portions thereof can also be embodied in programmable non-transitory storage media, for example, compact discs (CDs) or other discs including magnetic, optical, etc., readable by a machine or the like, or other computer usable storage media, including magnetic, optical, or semiconductor storage, or other source of electronic signals.

The processes (methods) and systems, including components thereof, herein have been described with exemplary reference to specific hardware and software. The processes (methods) have been described as exemplary, whereby specific steps and their order can be omitted and/or changed by persons of ordinary skill in the art to reduce these embodiments to practice without undue experimentation. The processes (methods) and systems have been described in a manner sufficient to enable persons of ordinary skill in the art to readily adapt other hardware and software as may be needed to reduce any of the embodiments to practice without undue experimentation and using conventional techniques.

To the extent that the appended claims have been drafted without multiple dependencies, this has been done only to accommodate formal requirements in jurisdictions which do not allow such multiple dependencies. It should be noted that all possible combinations of features which would be implied by rendering the claims multiply dependent are explicitly envisaged and should be considered part of the invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A system for use with a subject having a brain that includes a region responsible for visual perception, the system comprising:
   a first processing device configured for communicating with at least one nerve associated with at least one eye of the subject, the first processing device configured to:
      receive signals associated with first nerve impulses transmitted by the at least one nerve in response to viewing a scene by the at least one eye, and
      process the received signals by applying to the received signals at least one mapping that maps between nerve impulses and digital image data so as to produce generated digital image data representative of a visual perception, by the region of the brain, of the scene; and
   a second processing device configured for communicating with the region of the brain, the second processing device configured to:
      receive digital image data associated with the generated image data,
      process the received digital image data by applying to the received digital image data the at least one mapping so as to convert the received digital image data to second nerve impulses, and
      provide the second nerve impulses to the region of the brain such that the subject visually perceives the scene.

2. The system of claim 1, further comprising:
   an interfacing arrangement including:
      a first interface for placing the first processing device in communication with the at least one nerve, and
      a second interface for placing the second processing device in communication with the region of the brain.

3. The system of claim 2, wherein the first interface is operative to obtain the first nerve impulses transmitted by the at least one nerve in response to viewing the scene.

4. The system of claim 2, wherein the second interface is operative to provide the second nerve impulses to the region of the brain.

5. The system of claim 2, wherein at least a portion of the interfacing arrangement is configured to be implanted in the subject.

6. The system of claim 1, wherein at least one of the first or second processing devices is configured to be implanted in the subject.

7. The system of claim 1, wherein a communicative coupling is provided between the first and second processing devices, and wherein the second processing device is configured to receive digital image data from the first processing device via the communicative coupling.

8. The system of claim 7, wherein the communicative coupling between the first and second processing devices is a wireless connection.

9. The system of claim 7, wherein the communicative coupling between the first and second processing devices is a wired connection.

10. The system of claim 1, further comprising a server in network communication with the first and second processing devices, wherein the server is configured to: receive digital image data from the first processing device, and send the digital image data received from the first processing device to the second processing device.

11. The system of claim 1, wherein one of the first or second processing devices is further configured to generate the at least one mapping.

12. The system of claim 1, wherein the at least one mapping is generated at least in part by comparing a format of nerve impulses to one or more digital images.

13. The system of claim 1, wherein the at least one mapping provides a one-to-one mapping between nerve impulses and corresponding image data pixels or groups of image data pixels.

14. The system of claim 1, wherein the at least one mapping includes conversion parameters including image data attributes and corresponding nerve impulse encoding values.

15. The system of claim 1, wherein the digital image data received by the second processing device is the generated image data.

16. The system of claim 1, wherein the digital image data received by the second processing device is a modified version of the generated image data.

17. A method for use with a subject having a brain that includes a region responsible for visual perception, the system comprising:
   deploying a first processing device configured to be in communication with at least one nerve associated with at least one eye of the subject;
   deploying a second processing device configured to be in communication with the region of the brain;
   receiving, by the first processing device, signals associated with first nerve impulses transmitted by the at least one nerve in response to viewing a scene by the at least one eye;
   processing, by the first processing device, the received signals by applying to the received signals at least one mapping that maps between nerve impulses and digital image data so as to produce generated digital image data representative of a visual perception, by the region of the brain, of the scene;
   receiving, by the second processing device, digital image data associated with the generated image data;
   processing, by the second processing device, the received digital image data by applying to the received digital image data the at least one mapping so as to convert the received digital image data to second nerve impulses; and
   providing, by the second processing device, the second nerve impulses to the region of the brain such that the subject visually perceives the scene.

* * * * *